(12) United States Patent
Mehmood et al.

(10) Patent No.: US 9,672,990 B2
(45) Date of Patent: Jun. 6, 2017

(54) ORGANIC DYES INCORPORATING THE OXADIAZOLE MOIETY FOR EFFICIENT DYE-SENSITIZED SOLAR CELLS

(71) Applicant: King Fahd University of Petroleum and Minerals, Dhahran (SA)

(72) Inventors: Umer Mehmood, Dhahran (SA); Shakeel Ahmed, Dhahran (SA); Ibnelwaleed A. Hussein, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 14/718,040

(22) Filed: May 20, 2015

(65) Prior Publication Data
US 2016/0343515 A1    Nov. 24, 2016

(51) Int. Cl.
*H01G 9/20*      (2006.01)
*C07D 413/04*    (2006.01)
(Continued)

(52) U.S. Cl.
CPC ......... *H01G 9/2059* (2013.01); *C07D 271/04* (2013.01); *C07D 271/06* (2013.01);
(Continued)

(58) Field of Classification Search
CPC ............... H01L 51/007; H01L 51/0068; H01L 2051/0063; H01G 9/20–9/2059;
(Continued)

(56) References Cited

U.S. PATENT DOCUMENTS 3,404,161 A    10/1968 Strobel et al.
2003/0166943 A1*  9/2003 Kirsch ................. C07D 271/10
                                                         548/143
(Continued)

OTHER PUBLICATIONS

Wielopolski et al. "Harvesting UV photons for solar energy conversion applications." Phys.Chem.Chem.Phys., 2014, 16, 2090.*
(Continued)

*Primary Examiner* — James Lin
*Assistant Examiner* — Liesl C Baumann
(74) *Attorney, Agent, or Firm* — Oblon, McClelland, Maier & Neustadt, L.L.P.

(57) ABSTRACT

An oxadiazole dye for use as an organic photosensitizer. The oxadiazole dye comprising donor-π-spacer-acceptor type molecules in which at least one of an oxadiazole group acts as a π-conjugated bridge (spacer), a naphthyl unit acts as an electron-donating unit, a carboxyl group act as an electron acceptor group, and a cyano group acts as an anchor group. An optional thiophene group acts as part of the π-conjugated bridge (spacer). The dye for use as organic photosensitizers in a dye-sensitized solar cell. The dye for use in photodynamic therapies. Computational DFT and time dependent DFT (TD-DFT) modeling techniques showing Light Harvesting Efficiency (LHE), Free Energy for Electron Injection ($\Delta G^{inject}$), Excitation Energies, and Frontier Molecular Orbitals (FMOs) indicate that the series of dye comprise a more negative $\Delta G^{inject}$ and a higher LHE value; resulting in a higher incident photon to current efficiency (IPCE).

13 Claims, 3 Drawing Sheets

(51) Int. Cl.
*C07D 271/10* (2006.01)
*C07D 271/04* (2006.01)
*C07D 271/06* (2006.01)
*C07D 271/08* (2006.01)
*H01L 51/00* (2006.01)

(52) U.S. Cl.
CPC ......... *C07D 271/08* (2013.01); *C07D 271/10* (2013.01); *C07D 413/04* (2013.01); *H01L 51/007* (2013.01); *H01L 51/0068* (2013.01); *H01L 2051/0063* (2013.01)

(58) Field of Classification Search
CPC .. Y02E 10/542; C07D 271/04; C07D 271/06; C07D 271/08; C07D 271/10; C07D 271/107; C07D 271/113; C07D 413/04; C07C 57/04; C07C 57/54; C07C 69/54; C07C 69/653
See application file for complete search history.

(56) References Cited

U.S. PATENT DOCUMENTS

2008/0087325 A1\* 4/2008 John .................. C07F 15/0053
136/263
2009/0044857 A1\* 2/2009 Shigaki .............. C09B 23/0075
136/256

OTHER PUBLICATIONS

Yang et al. "Structure-property relationship of naphthalene based donor-pi-acceptor organic dyes for dye-sensitized solar cells: remarkable improvement of opencircuit photovoltage." J. Mater. Chem., 2012, 22, 22550.\*
Mehmood et al. "Theoretical study of benzene/thiophene based photosensitizers for dye sensitized solar cells (DSSCs)." Dyes and Pigments 118 (2015) 152-158.\*
Li et al. "Organic Sensitizers Featuring 9,10-Diaryl-Substituted Anthracene Unit." ACS Sustainable Chem. Eng. 2014, 2, 1776-1784.\*
Lin et al. "2,6-Conjugated anthracene sensitizers for high-performance dye-sensitized solar cells." Energy Environ. Sci., 2013, 6, 2477.\*
Lin et al. "Anthracene/Phenothiazine p-Conjugated Sensitizers for Dye-Sensitized Solar Cells using Redox Mediator in Organic and Water-based Solvents." ChemSusChem 2015, 8, 105-113.\*
Lin et al. "Anthracene based organic dipolar compounds for sensitized solar cells." Tetrahedron 70 (2014) 262-269.\*
Wenjie Fan, et al.; "Incorporation of Thiadiazole Derivatives as π-Spacer to Construct Efficient Metal-free Organic Dye Sensitizers for Dye-sensitized Solar cells: A Theoretical Study"; Commun. Comput. Chem.; Apr. 2013; vol. 1, No. 2; pp. 152-170.
U.S. Appl. No. 14/720,287, filed May 22, 2015, Mehmood, et al.

\* cited by examiner

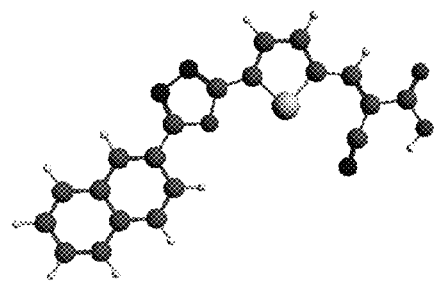
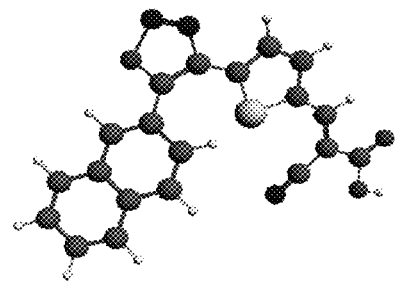
Figure 1a
Figure 1b
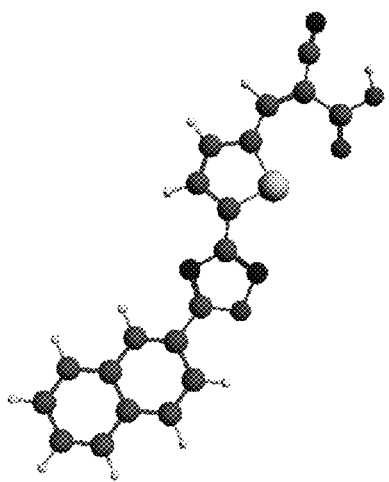
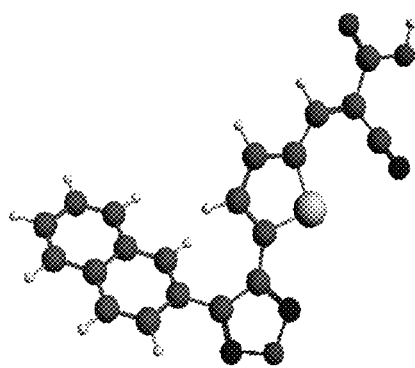
Figure 1c
Figure 1d

ORGANIC DYES INCORPORATING THE OXADIAZOLE MOIETY FOR EFFICIENT DYE-SENSITIZED SOLAR CELLS

FIELD OF THE INVENTION

The present invention relates to organic light absorbing compounds comprising at least one substituted oxadiazole group and at least one naphthyl group, and dye sensitized solar cells containing one or more of the light absorbing compounds. The invention includes the use of the organic light absorbing compounds as photosensitizers, or dyes, in a dye sensitized photoelectric transformation element such as a dye-sensitized solar cell (DSSC). The invention includes the use of the organic light absorbing compounds as a photosensitizer in a photodynamic therapy process.

BACKGROUND OF THE INVENTION

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Dye Sensitized Solar Cells (DSSCs), developed by O'Regan and Gratzel in 1991, are third-generation photovolatic devices which offer increased photoelectric transformation efficiencies at a low monetary cost. In contrast to silicon-based photovoltaic systems, where a semiconductor assumes both the tasks of light absorption and charge carrier transport, the configuration of a dye sensitized solar cell separates these functions.

Dye Sensitized Solar Cells (DSSCs) are unique in their functions in that they mimic the naturally occurring photosynthetic process found in plants and green algae. DSSCs utilize chromophores, similar to a photosynthetic system's porphyrins, in order to generate photosensitive charges which convert sunlight to energy. When subjected to light of an appropriate wavelength, these chromophores, as part of a dye molecule, are photochemically excited, and serve as the basis for conversion of sunlight into electrical energy.

Structurally, a dye sensitized solar cell (DSSC) has four main components which include 1) an optically transparent electrode (anode); 2) an organic, or organometallic, molecule (known as a dye or photosensitizer) adsorbed on a semiconductor oxide; 3) a liquid inorganic electrolyte or a solid organic hole-transporting material; and 4) a counter-electrode (cathode). The anode and cathode are arranged in a sandwich-like configuration, and the electrolyte is inserted between the two electrodes.

For a DSSC to operate the dye must allow electrons to move to an orbital with a higher energy (a dye excited state). The movement of these electrons result in the occurrence of a charge separation at the interface of the dye (now sensitized) and the semiconductor oxide components. This charge separation occurs via a photo-induced electron injection from the dye into the conduction band of the semiconductor oxide (i.e. titanium dioxide), leaving the dye molecules in an oxidized form. The electrons are then collected on a transparent conductive layer, and reach the counter-electrode (cathode) through an external electric circuit. The oxidized molecules of the dye are then regenerated through a transfer, such as one catalyzed by platinum (Pt), deposited on a cathode. Herein, the electrons trigger a series of redox reactions mediated through a redox pair which acts as an electrolyte. At the end of the reactions, the redox pair, now in a reduced form, transfers an electron to the dye, (which was held in an oxidized form), subsequently regenerating it and closing the cycle.

In addition to their reduced production costs and potential for achieving high energy-conversion efficiencies ($\eta$). Dye sensitized solar cells (DSSCs) have also attracted considerable attention for their flexibility, semi-transparancy, and stability during both prolonged light and thermal stresses. DSSCs have a greater independence on the angle of incident light needed to operate, as well as a high response to low level lighting conditions. As such, DSSCs tend to outperform conventional silicon photovoltaic devices under diffuse lighting conditions, such as those found in shady areas, on cloudy and/or rainy days, or even indoors with ambient lighting conditions. Indoor applications for DSSCs include their incorporation into a variety of devices such as, but not limited to, cell phones, laptop computers, and ipads. DSSCs may also be utilized in conventional solar arrays, or for building-integrated photovoltaic products such as windows, skylights, solar tubes, and siding.

For solar cells to attain the desired high level of photoelectric transformation efficiency ($\eta$), the dye component should possess a wide absorption spectrum (of solar light), as well as a high molar extinction coefficient ($\epsilon$). Consequently, photoelectric transformation efficiency is primarily determined by the number of collected and injected photons, and thus by the light absorbed by the dye or photosensitizer. Additionally, for an efficient electron injection, the dye must be able to absorb (by chemisorption) onto the surface of the semiconductor, and upon photoexcitation, inject electrons into the conduction band of the semiconductor with a quantum yield of unity. As known in the art, the 'quantum yield of unity' is useful in modeling photosynthesis, where $Q_D = Q_A = 1$.

Currently, the most successful and widely-used dyes are organometallic compounds based on ruthenium $2^+$ complexes [Ru(II)]. These dyes have allowed photoelectric transformation efficiencies ($\eta$) of 11% to be reached. However, despite their efficiency, ruthenium compounds have a variety of disadvantages. One concern is the low molar extinction coefficient ($\epsilon$) inherent to derivatives of ruthenium [Ru(II)]. Other shortcomings involve the expensive and complex synthesis and purification phases which ultimately result in a product having a limited chemical stability.

Further still, the photo-active regions of photovoltaic devices employing ruthenium complex dyes are reduced to the visible part of the solar spectrum, and within that, to the shorter wavelength regions. Consequently, photons of the longer wavelength regions are not harvested, and cannot be converted into electrical energy. Therefore, it is desirable to extend the photo-response of a dye into the longer wavelength regions of the solar spectrum so as to improve the overall light-to-electricity conversion efficiency of a DSSC. As synthetic modifications of ruthenium complexes have been carried out with limited success, the development of alternative dyes with wider absorption bands falling within the longer wavelength regions of the solar spectrum has garnered a greater interest.

Metal-free organic dyes present one such alternative dye. As a group, they present advantages over organometallic dyes for use in DSSCs including, but not limited to: (1) possessing high molar extinction coefficients ($\epsilon$), (2) having simpler and less expensive synthesis processes, and (3) the existence of a chemical industry already capable of carrying out a large scale synthesis process.

The structural arrangement of metal-free organic dye sensitizers is most often of the linear D-π-A type. Therein, 'D' is an electron donor group (i.e. electron-rich), 'π' is an unsaturated spacer having π-conjugated bonds and 'A' is an electron acceptor group (i.e. electron-poor group). Customarily, the electron acceptor group is further coupled with a group which allows for the anchoring (i.e. adsorption) of the dye molecule onto a surface such as titanium dioxide. The D-π-A system allows for a variety of modifications to be made to the dye by varying the D, π-spacer, and/or A groups.

For most metal-free organic dyes, arylamine derivatives function as the electron-donor group (D). These typically include groups of the triarylamine type ($NAr_3$). A cyanoacrylic acid or rhodamine residue typically functions as an electron acceptor group A, while the π spacer is often based on thiophene structures, such as a fused monocyclic and/or polycyclic thiophene ring(s). With regard to the anchoring group, many organic dyes reporting good efficiencies have an anchoring group comprising an acrylic acid group. Often, a combination of the electron acceptor group 'A' and the anchor group include a 2-cyanoacrylate group. However, in the design of functional and efficient dye molecules, other groups should be considered for the D, π, and A groups.

The electrical and optical properties of π-conjugated organic molecules are linked to a parameter known as the HOMO-LUMO gap (Eg). This corresponds to the energy difference between the Highest Occupied Molecular Orbital (HOMO) and the Lowest Unoccupied Molecular Orbital (LUMO). The energy difference between the HOMO and LUMO levels is approximately equal to the 'band gap energy' as defined for collections of molecules in a thin-film. This difference in value, given relative to the Fermi level and in units of Hartree, may serve as a measure of the excitability of a molecule. For example, the smaller the energy, the more easily the molecule will be excited. In order to be used in optoelectronics, including DSSCs, or photodynamic therapies, this band gap energy should be as low as possible.

It is also important to realize that many molecules presenting a low Eg gap are often those in possession of higher dimensions. These 'high dimension molecules' tend to, by virtue of their bulky structure, be weakly soluble, thus limiting their role in photovoltaic devices. Additionally, larger dimension molecules have been associated with greater toxicity, or health, risks to those individuals exposed to them. Therefore, it is important to find new light absorbing π-conjugated molecules (D-π-A) that present a low Eg gap, are soluble in a preferred solvent (i.e. an organic medium and/or water), and are non-toxic to humans and animals.

In summary, an important strategy for realizing a high photoelectric conversion efficiency is to allow for light of a long wavelength to be absorbed by the dye molecule, along with chromophore and π spacer group combinations which render a low HOMO-LUMO gap in the dye molecule as well.

In order to evaluate any proposed dye candidates, their properties, such as 'band-gap energy' should be determined. Dye energies, based upon the HOMO and LUMO value, can be established experimentally by means of cyclic voltammetry (CV), X-ray photoelectron spectroscopy (XPS) or ultraviolet photoelectron spectroscopy (UPS). Dye energies can also be calculated by means of quantum-mechanical methods, for example, by means of dependent density functional theory and/or time-dependent density functional theory (DFT/TD-DFT). Theoretical DFT/TD-DFT can suggest which dyes will have the greatest efficiencies prior to exploration of synthesis routes. Therefore, investigation into alternative D, π-spacer, and A groups is proceeding, with both theoretical and physical approaches, in order to determine dye energies and light harvesting efficiencies of candidate dye molecules.

In this regard, density functional theory/time dependent density functional theory (DFT/TD-DFT) is an effective tool for investigating the ground and excited state properties of photosensitizer complexes as compared to other high level quantum approaches. The DFT approach is, in principle, exact, with DFT/TD-DFT computed orbitals deemed suitable for a typical molecular orbital theoretical analysis and interpretation. Furthermore, DFT/TD-DFT fundamental scaling properties do not deteriorate when the methodological precision is increased.

Most dyes absorb light in the same range as a commonly used red-dye (below 600 nm). Thus photons of the longer wavelength region(s) are still lost to photoconversion. As the spectrum of solar radiation at ground level has an emission peak that extends from approximately 500 nm to approximately 650 nm, the use of dyes that have absorption peaks in this region of the spectrum are greatly needed. Dyes prepared to date either absorb below 500 nm, or above 650 nm, and therefore do not capture most of the solar radiation. A second drawback is that these dyes exhibit low molar extinction coefficients.

Other roles exist for light absorbing molecules, such as those photosensitizers which have been developed for DSSCs. These molecules may also play a role in treating medical conditions through a course of treatment known as phototherapy. Photodynamic therapy involves a minimally invasive two-step process wherein a photosensitizer is administered and, once it has permeated a target tissue, the photosensitizer is then activated by exposure to a dose of electromagnetic (usually light) radiation at a particular wavelength. Photodynamic therapies have been used to treat a number of conditions including the treatment of malignant skin cells, (ie basal cell carcinoma), age-related macular degeneration, actinic keratosis and hair loss.

More specifically, photodynamic therapy (PDT) is a form of phototherapy which uses nontoxic light-sensitive compounds that are exposed selectively to light, whereupon they cause a reduction in targeted hyperproliferative, malignant, and/or diseased cells. PTD may also result in the stimulus of hair growth. Key requirements for the design of effective phototherapeutic agents include, but are not limited to, having an efficient energy or electron transfer to cellular components, a low tendency to aggregate when placed in a solvent delivery system, an efficient and selective targeting of a desired tissue, a low systemic toxicity, and a lack of mutagenicity.

One phototherapy mechanism pathway occurs via the direct energy or electron transfer from a photosensitizer to a targeted cellular component(s) thereby causing cellular death or necrosis. The wavelength of the light source is required to be of an appropriate wavelength so as to excite the photosensitizer dye in order to destroy any tissues which have selectively taken up the photosensitizer and have been locally exposed to light. Malignant and other diseased cells of the skin (i.e. the epidermal, dermal and hypodermal layers) are the most accessible to light and can therefore be treated using photodynamic therapy with the greatest ease. As red light has a penetration of about 1 cm in living tissues, malignant and/or diseased cells on or near the surface of the skin can most preferably be treated with this wavelength of light.

Wavelengths of light in the near infrared region (NIR region 750 nm-950 nm) provide radiation which penetrates more deeply in the skin. Therefore, in order to treat malignant or diseased tissues which require a higher penetration of light into the body, the photosensitizer should absorb in these higher wavelengths. Also, as with the use of photosensitizers for DSSCs, the HOMO-LUMO (Eg) gap of the dye molecule(s) for use in a photodynamic therapy process should also be as low as possible.

Therefore, there is a need to provide photosensitizers which are versatile, have a low HOMO-LUMO (Eg) gap, and absorb light in a wide spectrum of wavelengths. Those compounds having absorption in the visible, UV and/or NIR region, i.e. between 300 nm and 1000 nm are desired. The development of dye compounds which absorb radiations from 400 nm-950 nm is highly desirable due to the fact that this specific range of absorbance enables the use of the dye compounds in the field of electronics, photovoltaics, optoelectronics and photodynamic therapies. An organic dye should also be resistant to photogdegradation, and contain a reactive group capable of binding the dye stably to a surface such as that of a semiconductor, or in the case of phototherapy, a layer of the skin, so as to facilitate the transfer of electrons.

SUMMARY OF THE INVENTION

The present disclosure provides a light absorbing molecule, also referred to herein as a light absorbing compound, a photosensitizer, and a "dye", of the D-π-A (Donor-spacer-Acceptor) type and a dye sensitized solar cell (DSSC) containing the light absorbing molecule. The dye as disclosed is an oxadiazole based photosensitizer for use, for example, in photovoltaic devices such as, but not limited to, dye-sensitized solar cells (DSSC). The dye provides a stable and soluble functional compound having absorption in the UV and visible wavelength regions of the solar spectrum. A dye as disclosed herein may be used individually, or combined with a second dye, as disclosed herein, or with other known dyes, so as to cover a broad range of the solar spectrum. The light absorbing molecule disclosed herein may be tuned to provide a low bandgap and favorable energy level, and can be efficiently chemisorbed to a nanoporous surface of a photoactive layer in a DSSC structure or device. In addition to its use in photovoltaic devices, the light absorbing molecule disclosed herein can be used in the fields of optoelectronics, photonics, and photodynamic therapies. In some embodiments the light absorbing molecule contains few atoms and absorbs in the longer wavelength regions of light thus presenting a good photodynamic therapy dye candidate. Photodynamic therapy may be useful in treating a hyperproliferative, cancerous, or diseased tissue.

In a first embodiment the light absorbing molecule of the present disclosure is an organic light absorbing molecule of formula (I), including the tautomers thereof:

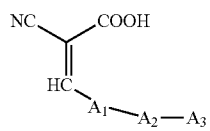
(I)

wherein $A_1$ is a divalent thiophene group of formula (I')

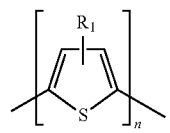
(I')

wherein R1 is H, OH, C1-C6 alkyl, Cl, Br, F, or I, and n=0-5; preferably n=1-5;

$A_2$ is at least one divalent 5-membered heterocyclic group selected from the group consisting of

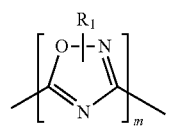
(II')

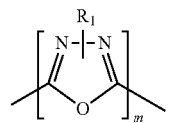
(III')

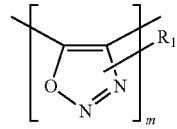
(IV')

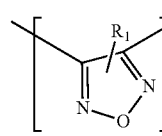
(V')

wherein $R_1$ is H, OH, C1-C6 alkyl, Cl, Br, F, or I and m=1-5;

$A_3$ is at least one polycyclic aromatic hydrocarbon chromophore, preferably selected from the group consisting of

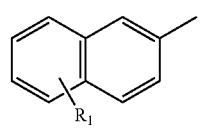
(VI')

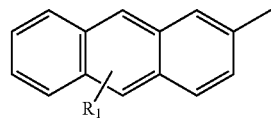
(VII')

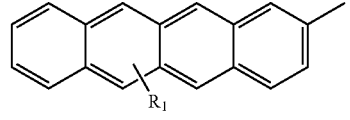
(VIII')

wherein $R_1$ is H, OH, C1-C6 alkyl, Cl, Br, F, or I

In a further embodiment the organic light absorbing molecule of the present disclosure may be in the form of an (E) or (Z) configuration isomer.

In a preferred embodiment the organic light absorbing molecule comprises a substituted cyanoacrylic acid selected from the group consisting of:

(E)-2-Cyano-3-(5-(5-(naphthalen-2-yl)-1,3,4-oxadiazol-2-yl)thiophen-2-yl)-acrylic acid;

(E)-2-Cyano-3-(5-(5-(naphthalen-2-yl)-1,2,3-oxadiazol-4-yl)thiophen-2-yl)-acrylic acid;

(E)-2-Cyano-3-(5-(5-(naphthalen-2-yl)-1,2,4-oxadiazol-3-yl)thiophen-2yl)-acrylic acid;

(E)-2-Cyano-3-(5-(4-(naphthalen-2-yl)-1,2,5-oxadiazol-3-yl)thiophen-2yl)-acrylic acid;

(E)-2-Cyano-3-(5-(naphthalen-2-yl)-1,3,4-oxadiazol-2-yl)-acrylic acid;

(E)-2-Cyano-3-(5-(naphthalen-2-yl)-1,2,3-oxadiazol-4-yl)-acrylic acid;

(E)-2-Cyano-3-(5-(naphthalen-2-yl)-1,2,4-oxadiazol-3-yl)-acrylic acid;

(E)-2-Cyano-3-(4-(naphthalen-2-yl)-1,2,5-oxadiazol-3-yl)-acrylic acid;

and (Z)-2-Cyano-3-(5-(5-(naphthalen-2-yl)-1,3,4-oxadiazol-2-yl)thiophen-2-yl)-acrylic acid;

(Z)-2-Cyano-3-(5-(5-(naphthalen-2-yl)-1,2,3-oxadiazol-4-yl)thiophen-2-yl)-acrylic acid;

(Z)-2-Cyano-3-(5-(5-(naphthalen-2-yl)-1,2,4-oxadiazol-3-yl)thiophen-2yl)-acrylic acid;

(Z)-2-Cyano-3-(5-(4-(naphthalen-2-yl)-1,2,5-oxadiazol-3-yl)thiophen-2yl)-acrylic acid;

(Z)-2-Cyano-3-(5-(naphthalen-2-yl)-1,3,4-oxadiazol-2-yl)-acrylic acid;

(Z)-2-Cyano-3-(5-(naphthalen-2-yl)-1,2,3-oxadiazol-4-yl)-acrylic acid;

(Z)-2-Cyano-3-(5-(naphthalen-2-yl)-1,2,4-oxadiazol-3-yl)-acrylic acid;

(Z)-2-Cyano-3-(4-(naphthalen-2-yl)-1,2,5-oxadiazol-3-yl)-acrylic acid;

including the tautomers thereof.

In a preferred embodiment the organic light absorbing molecule comprises a substituted cyanoacrylic acid selected from the group consisting of:

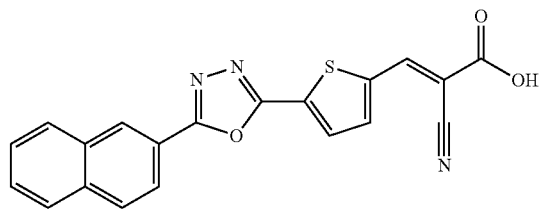

(Ia)

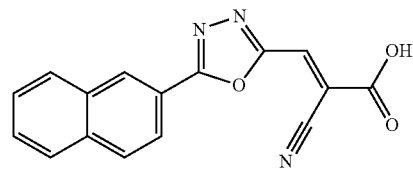

(Ib)

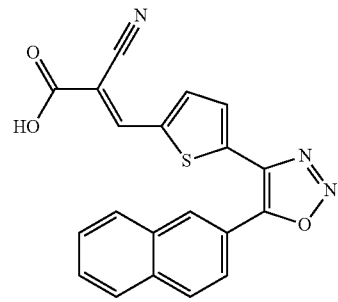

(IIa)

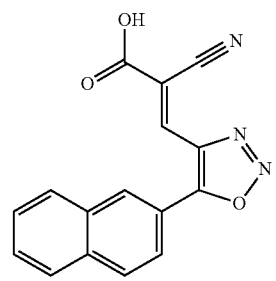

(IIb)

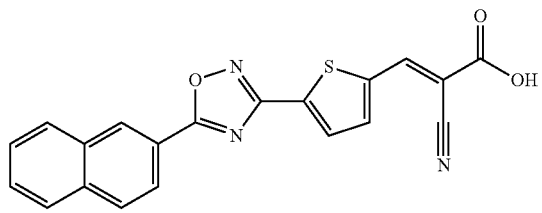

(IIIa)

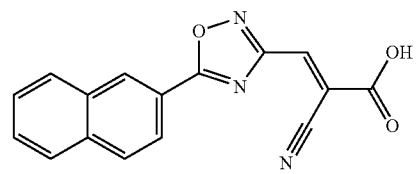

(IIIb)

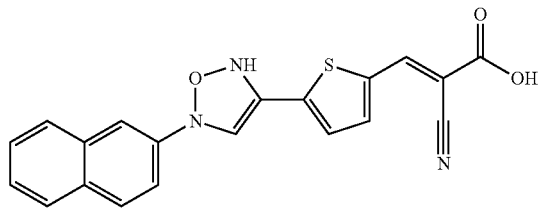

(E)-2-cyano-3-(5-(5-naphthalen-2-yl)-1,2,5-oxadiazol-3-yl)thiophen-2-yl)cyanoacrylic acid

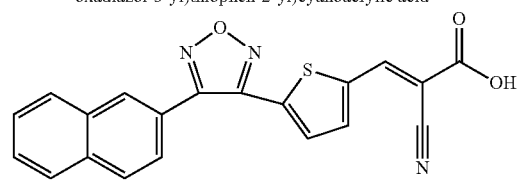

(E)-2-cyano-3-(5-(4-(naphthalen-2-yl)-1,2,5-oxadiazol-3-yl)thiophen-2-yl)acrylic acid

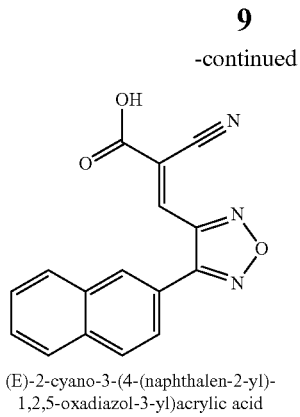

(E)-2-cyano-3-(4-(naphthalen-2-yl)-
1,2,5-oxadiazol-3-yl)acrylic acid

In a further embodiment, at least one of $-A_1$, or at least one of $-A_1-A_2$, forms a conjugated system with the adjacent aromatic hydrocarbon chromophore of formula (VI'), (VII'), or (VIII').

In another embodiment the organic light absorbing molecule of formula (I) comprises a cyanoacrylic acid wherein a —COOH group of the cyanoacrylic acid is covalently coupled to a surface, for example as a —COO⁻ group.

In a further embodiment the surface is a photoactive semiconductor layer, or a layer of an animal skin selected from the group consisting of an epidermis, a dermis and a hypodermis.

In a preferred embodiment the surface is a photoactive semiconductor layer comprising titanium dioxide.

In a further embodiment the organic light absorbing molecule of formula (I) absorbs at least one wavelength of IR, visible, or UV light.

In another embodiment the disclosure includes a dye sensitized solar sell comprising an organic light absorbing molecule of formula (I).

In a further embodiment the disclosure includes a dye represented by formula (II):

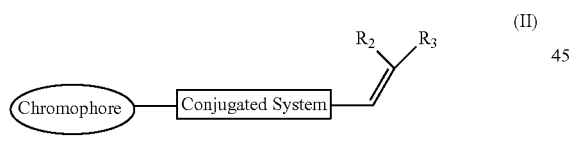

(II)

wherein the chromophore is an organic moiety able to absorb at least one of IR, UV and/or visible light when coupled with the conjugated system selected from the group consisting of:

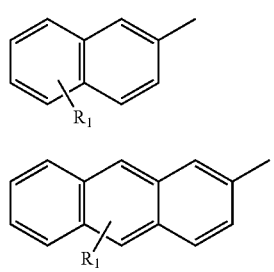

(VI')

(VII')

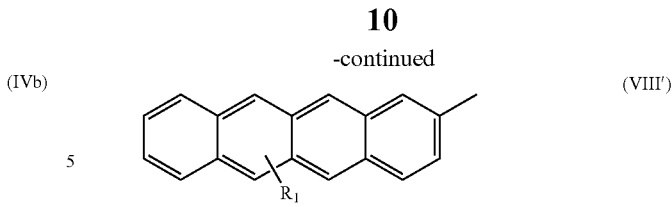

(VIII')

wherein $R_1$ is H, OH, $C_1$-$C_6$ alkyl, Cl, Br, F, or I;
wherein the conjugated system comprises a divalent thiophene group of formula (I')

(I')

wherein $R_1$ is H, OH, $C_1$-$C_6$ alkyl, Cl, Br, F, or I and n=0-5; preferably n=1-5;

and at least one a divalent 5-membered heterocyclic group selected from the group consisting of

(II')

(III')

(IV')

(V')

wherein $R_1$ is H, OH, $C_1$-$C_6$ alkyl, Cl, Br, F, or I and m=1-5;

wherein $R_2$ is selected from the group comprising H, —CN, and —NO₂, preferably —CN, and wherein $R_3$ is selected from —COOH, —SO₃H, —PO₃H₂, and —BO₂H₂, preferably —COOH.

In a further embodiment the dye represented by formula II the chromophore has an independent absorption in the range of 200-300 nm when uncoupled to the conjugated system; and a first absorption in the wavelength range of 326 nm-500 nm, for example and including in the range of 350 nm-450 nm, and a second absorption in the range of 472-700 nm, for example and including 500-650 nm when coupled with the conjugated system.

In a further embodiment the dye represented by formula (II) is chemisorbed to a photoactive semiconductor layer of a DSSC, or a dermal layer of an animal skin selected from the group consisting of an epidermis, a dermis and a hypodermis.

In a preferred embodiment the dye represented by formula (II) is chemisorbed to a photoactive semiconductor layer comprising titanium dioxide.

In a further embodiment the disclosure includes a dye sensitized photoelectric transformation element comprising at least one organic dye of formula (II).

In a further embodiment the disclosure includes a photoelectric conversion device comprising at least one of a passive substrate, wherein the passive substrate comprises:
a conductive layer;
a light absorbing layer
an intermediate layer; and
a counter electrode;
further wherein the light absorbing layer comprises a dye selected from the group consisting of
(E)-2-Cyano-3-(5-(5-(naphthalen-2-yl)-1,3,4-oxadiazol-2-yl)thiophen-2-yl)-acrylic acid;
(E)-2-Cyano-3-(5-(5-(naphthalen-2-yl)-1,2,3-oxadiazol-4-yl)thiophen-2-yl)-acrylic acid;
(E)-2-Cyano-3-(5-(5-(naphthalen-2-yl)-1,2,4-oxadiazol-3-yl)thiophen-2yl)-acrylic acid;
(E)-2-Cyano-3-(5-(4-(naphthalen-2-yl)-1,2,5-oxadiazol-3-yl)thiophen-2yl)-acrylic acid;
(E)-2-Cyano-3-(5-(naphthalen-2-yl)-1,3,4-oxadiazol-2-yl)-acrylic acid;
(E)-2-Cyano-3-(5-(naphthalen-2-yl)-1,2,3-oxadiazol-4-yl)-acrylic acid;
(E)-2-Cyano-3-(5-(naphthalen-2-yl)-1,2,4-oxadiazol-3-yl)-acrylic acid;
(E)-2-Cyano-3-(4-(naphthalen-2-yl)-1,2,5-oxadiazol-3-yl)-acrylic acid;
and
(Z)-2-Cyano-3-(5-(5-(naphthalen-2-yl)-1,3,4-oxadiazol-2-yl)thiophen-2-yl)-acrylic acid;
(Z)-2-Cyano-3-(5-(5-(naphthalen-2-yl)-1,2,3-oxadiazol-4-yl)thiophen-2-yl)-acrylic acid;
(Z)-2-Cyano-3-(5-(5-(naphthalen-2-yl)-1,2,4-oxadiazol-3-yl)thiophen-2yl)-acrylic acid;
(Z)-2-Cyano-3-(5-(4-(naphthalen-2-yl)-1,2,5-oxadiazol-3-yl)thiophen-2yl)-acrylic acid;
(Z)-2-Cyano-3-(5-(naphthalen-2-yl)-1,3,4-oxadiazol-2-yl)-acrylic acid;
(Z)-2-Cyano-3-(5-(naphthalen-2-yl)-1,2,3-oxadiazol-4-yl)-acrylic acid;
(Z)-2-Cyano-3-(5-(naphthalen-2-yl)-1,2,4-oxadiazol-3-yl)-acrylic acid;
(Z)-2-Cyano-3-(4-(naphthalen-2-yl)-1,2,5-oxadiazol-3-yl)-acrylic acid;
including the tautomers thereof.

In a still further embodiment the disclosure includes a composition comprising a pharmaceutically acceptable medium and an oxadiazole compound selected from the group consisting of:
(E)-2-Cyano-3-(5-(5-(naphthalen-2-yl)-1,3,4-oxadiazol-2-yl)thiophen-2-yl)-acrylic acid;
(E)-2-Cyano-3-(5-(5-(naphthalen-2-yl)-1,2,3-oxadiazol-4-yl)thiophen-2-yl)-acrylic acid;
(E)-2-Cyano-3-(5-(5-(naphthalen-2-yl)-1,2,4-oxadiazol-3-yl)thiophen-2yl)-acrylic acid;
(E)-2-Cyano-3-(5-(4-(naphthalen-2-yl)-1,2,5-oxadiazol-3-yl)thiophen-2yl)-acrylic acid;
(E)-2-Cyano-3-(5-(naphthalen-2-yl)-1,3,4-oxadiazol-2-yl)-acrylic acid;
(E)-2-Cyano-3-(5-(naphthalen-2-yl)-1,2,3-oxadiazol-4-yl)-acrylic acid;
(E)-2-Cyano-3-(5-(naphthalen-2-yl)-1,2,4-oxadiazol-3-yl)-acrylic acid;
(E)-2-Cyano-3-(4-(naphthalen-2-yl)-1,2,5-oxadiazol-3-yl)-acrylic acid;
and
(Z)-2-Cyano-3-(5-(5-(naphthalen-2-yl)-1,3,4-oxadiazol-2-yl)thiophen-2-yl)-acrylic acid;
(Z)-2-Cyano-3-(5-(5-(naphthalen-2-yl)-1,2,3-oxadiazol-4-yl)thiophen-2-yl)-acrylic acid;
(Z)-2-Cyano-3-(5-(5-(naphthalen-2-yl)-1,2,4-oxadiazol-3-yl)thiophen-2yl)-acrylic acid;
(Z)-2-Cyano-3-(5-(4-(naphthalen-2-yl)-1,2,5-oxadiazol-3-yl)thiophen-2yl)-acrylic acid;
(Z)-2-Cyano-3-(5-(naphthalen-2-yl)-1,3,4-oxadiazol-2-yl)-acrylic acid;
(Z)-2-Cyano-3-(5-(naphthalen-2-yl)-1,2,3-oxadiazol-4-yl)-acrylic acid;
(Z)-2-Cyano-3-(5-(naphthalen-2-yl)-1,2,4-oxadiazol-3-yl)-acrylic acid;
(Z)-2-Cyano-3-(4-(naphthalen-2-yl)-1,2,5-oxadiazol-3-yl)-acrylic acid;
including the tautomers thereof.

In a further embodiment the disclosure includes a method of photodynamic therapy for treating a hypo- or hyper-proliferative, malignant and/or diseased tissue in a subject in need thereof, comprising: (i) administering to the hypo- or hyper-proliferative, malignant and/or diseased tissue of the subject an oxadiazole compound selected from the compounds as disclosed herein including the tautomers thereof and/or a pharmaceutically acceptable conjugate thereof that associates with the tissue so as to form a target tissue, and (ii) irradiating the target tissue with a light of a wavelength and intensity sufficient to activate the oxadiazole compound, so as to destroy, or decrease in size, the hyperproliferative, malignant, and/or diseased tissue, or to stimulate a hypoproliferative tissue.

In a further embodiment, the hypo- or hyper-proliferative, malignant and/or diseased tissue is selected from the group consisting of a hyperproliferative, malignant, and/or diseased epidermal, dermal, and/or hypodermal tissue.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1a-d shows the (E) structure of each of the dye (Ia, IIa, Ma, IVa) comprising an oxadiazole isomer and a thiophene group. FIG. 1a shows dye (Ia); FIG. 1b shows dye (IIa); FIG. 1c shows dye (Ma); and FIG. 1d shows dye (IVa).

DETAILED DESCRIPTION OF THE INVENTION

Figure 2:
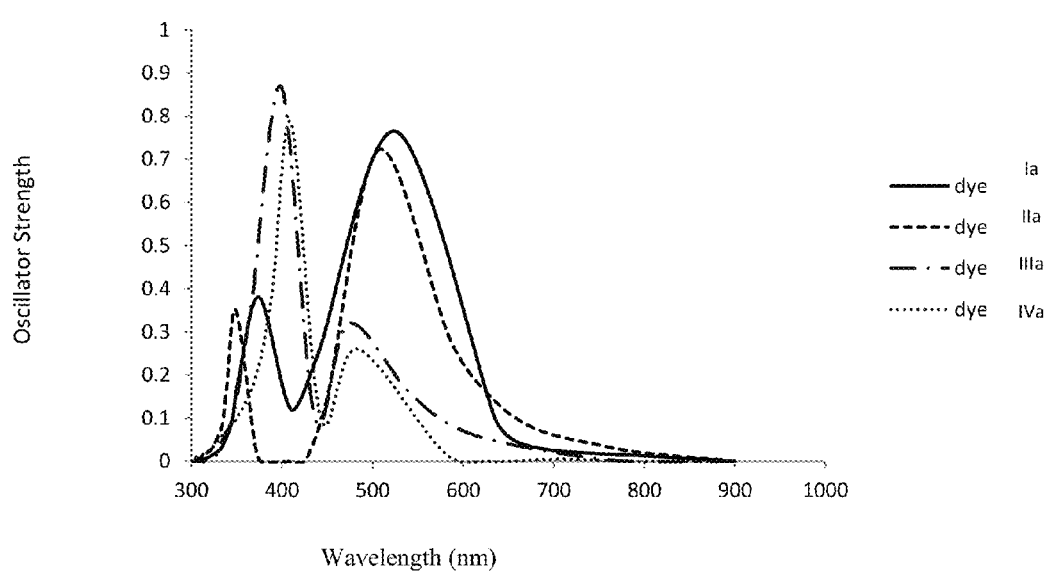
FIG. 2 shows a simulated absorption spectra of the (E) structure of each of the dye (Ia, IIa, IIIa, IVa) comprising an oxadiazole isomer, a naphthyl group and a thiophene group.

In a preferred embodiment the disclosure is drawn to a light absorbing molecule of the D-π-A (Donor-spacer-Acceptor) type incorporating an oxadiazole moiety. The light absorbing molecule is preferably for use in a photovoltaic device, such as a dye-sensitized solar cell, or for use in photodynamic therapies.

The term 'light absorbing molecule as used herein is meant to be interchangable with the term 'light absorbing compound' and both of these terms as presented herein are meant to be interchangable with the term photosensitizer.

The term "anchoring group", as used herein, is meant to refer to any functional group that allows a covalent coupling, which may also be referred to as chemisorption of the entity to which such anchoring group belongs, to a surface, for example the surface of a nanoporous semiconductor layer within a solar cell.

A "chromophore" as used herein is functional group within a molecular structure that is responsible for the light absorption. A "conjugated system" as used herein is a heteroaromatic molecule or portion of a molecule having alternating double bonds and single bonds between atom centers. The term "molecular structure", as used herein, refers to the structure of a molecule. For example, the "molecular structure of a dye" is the structure of the molecule of the dye. An "anchoring group" that is included in the molecular structure of a dye forms part of the molecular structure.

Herein, a dye is referred to as being "chemisorbed" to a layer or surface, if the dye is covalently coupled thereto. The term "covalent coupling", as used herein, is interchangeable with the term "chemisorption".

The term "a dye including an anchoring group in its molecular structure" as used herein, may have more than one anchoring group(s) present within the structure.

The term "a molecule that is able to absorb in the wavelength range of UV and/or visible and/or IR light" as used herein, refers to a molecule that is able to absorb light in one or in several regions of the wavelength range(s) indicated, or furthermore, over the total regions of the given wavelength range(s). For example a molecule may absorb in the range of from 250 nm-500 nm, whereas another molecule may absorb in the range of from 700 nm-1000 nm, whereas a third molecule may absorb in the range of from 250-1000 nm.

The term photoelectric transformation element is meant to comprise materials that allow photoelectric transformation, or conversion to take place in a device, such as a dye sensitized solar cell.

The light absorbing compounds disclosed herein are characterized by the presence of an electron-donating group (D) at one end of the dye compound, and an electron-accepting group (A) at the other end of the dye compound, where (A) and (D) are linked by a π conjugated system. The introduction of a strong electron-withdrawing group such as a cyanoacrylate group into the electron-donating backbone of the light absorbing compound results in a longer wavelength absorbance by lowering the LUMO level to thereby desirably provide a high photoelectric conversion efficiency.

The light absorbing compounds are designed and prepared by introducing an oxadiazole group as a π-conjugated bridge between donor and acceptor moieties. In the resulting light absorbing compounds a naphthyl unit acts as an electron-donating moiety and carboxyl and cyano groups (—COOH and —CN) act as electron acceptor and anchor groups, respectively.

Referring now to the drawings, wherein like reference numerals designate identical or corresponding parts throughout the several views.

FIG. 1a shows the (E) structure of dye (Ia) comprising an oxadiazole isomer and a thiophene group. FIG. 1b shows the (E) structure of dye (IIa) comprising an oxadiazole isomer and a thiophene group. FIG. 1c shows the (E) structure of dye (IIIa) comprising an oxadiazole isomer and a thiophene group. FIG. 1d shows the (E) structure of dye (IVa) comprising an oxadiazole isomer and a thiophene group.

The dye molecules as disclosed herein have the general structure of Formula (X), including the tautomers thereof:

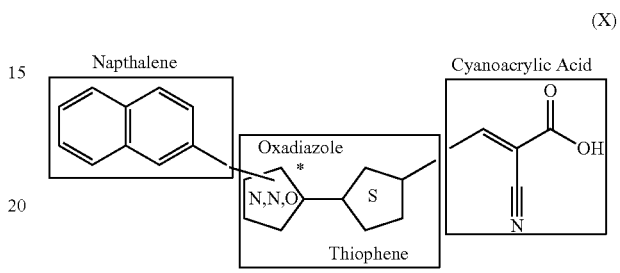

(X)

where * indicates the oxadiazole structures as shown below:

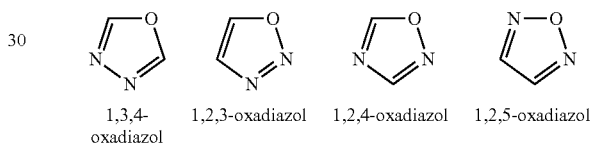

1,3,4-oxadiazol   1,2,3-oxadiazol   1,2,4-oxadiazol   1,2,5-oxadiazol

Other portions of the light absorbing compound include:

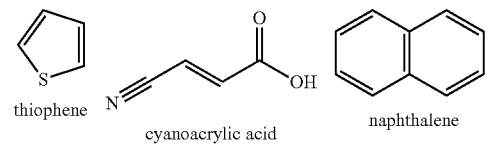

thiophene   cyanoacrylic acid   naphthalene

In one embodiment the thiophene group is an optional moiety in the dye molecules having the general structure of formula (X).

The structure of each of a series of oxadiazole based photosensitizers is shown below. The photosensitizers are described as being an (E) or (Z) configuration isomer of an organic light absorbing molecule of formula (I), including the valence tautomers thereof:

(I)

wherein A₁ is a divalent thiophene group of formula (I')

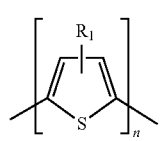
(I')

wherein R₁ is H, OH, C1-C6 alkyl, Cl, Br, F, or I, and n=0-5; preferably n=1-5;

A₂ is at least one divalent 5-membered heterocyclic group selected from the group consisting of

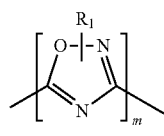
(II')

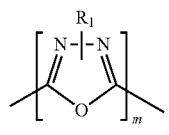
(III')

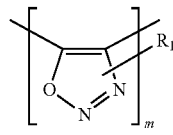
(IV')

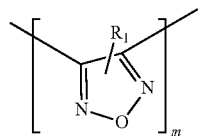
(V')

wherein R₁ is H, OH, C1-C6 alkyl, Cl, Br, F, or I, and m=1-5;

A₃ is an aromatic hydrocarbon chromophore; preferably selected from the group consisting of

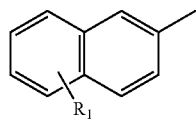
(VI')

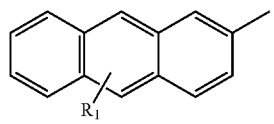
(VII')

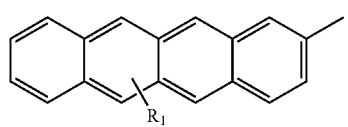
(VIII')

wherein R₁ is H, OH, C1-C6 alkyl, preferably —CH3, Cl, Br, F, or I. Each of the series of light absorbing compounds of the present disclosure comprise at least one of an anchoring group independently selected from the group consisting of —COOH, —SO₃H, —PO₃H₂, and —BO₂H₂, preferably —COOH. In one embodiment, the anchoring group is capable of bonding to a semiconductor electrode surface of an organic solar cell.

Each of the series of light absorbing compounds of the present disclosure also comprise an acceptor site selected from the group consisting of H, —CN, and —NO₂, preferably —CN. Together, these groups advantageously form a cyanoacrylate group that attracts electrons by an inductive effect.

The π-conjugated spacer comprises at least one divalent 5-membered hetercyclic oxadiazole group. In one embodiment, a divalent thiophene group is also present. These groups may be represented by the formula: -(A¹)(-A²)-, wherein A¹ and A² each independently represent the thiophene and oxadiazole substituents, respectively. Furthermore, the π-conjugated spacer has, as a constituent atom thereof, a heteroatom that forms a double bond with carbon in the end region—on the side of the anchor backbone—and is coordinate-bonded thereto.

According to the present disclosure, the donor group comprises an aromatic hydrocarbon as a chromophore. In one embodiment, the aromatic hydrocarbon chromophore is a naphthyl group.

The compounds of the present disclosure may also be described as a dye represented by formula (II):

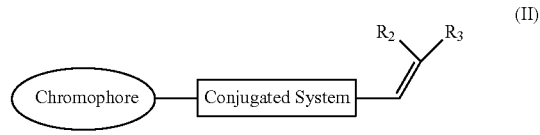
(II)

wherein the chromophore is an organic molecule able to absorb in the wavelength range of IR, UV and/or Visible light when coupled with the conjugated system, such as one selected from the group consisting of:

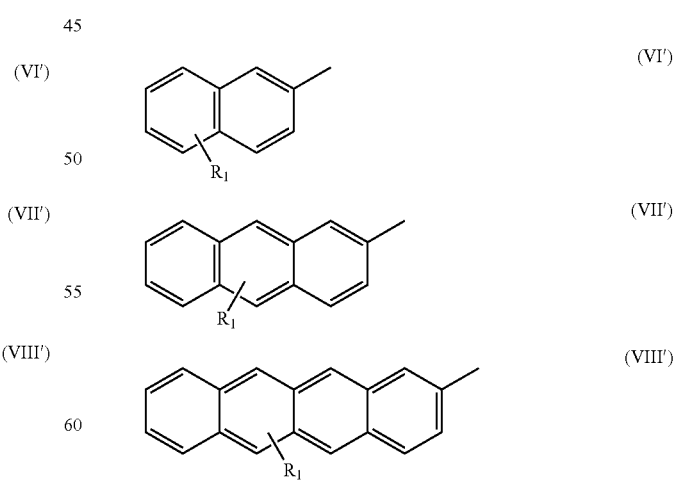

wherein R₁ is H, OH, C1-C6 alkyl, Cl, Br, F, or I;

wherein the conjugated system comprises a divalent thiophene group of formula (I')

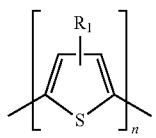

(I')

wherein R₁ is H, OH, CH₃, Cl, Br, F, or I, and n=0-5;

and at least one of a divalent 5-membered heterocyclic group selected from the group consisting of

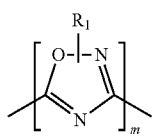

(II')

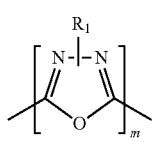

(III')

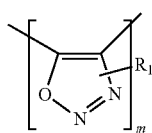

(IV')

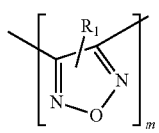

(V')

wherein R₁ is H, OH, C1-C6 alkyl, Cl, Br, F, or I and m=1-5;

wherein R₂ is selected from the group comprising H, —CN, and —NO₂, preferably —CN, and wherein R₃ is selected from —COOH, —SO₃H, —PO₃H₂, and —BO₂H₂, preferably —COOH.

Preferably the light absorbing compounds are not substituted with any primary, secondary or tertiary amine.

The light absorbing compounds may hereinafter simply be referred to as the compounds of the present disclosure.

The compounds of the present disclosure present a low H-L gap energy, in addition to having a donor site comprising an electron-donating backbone at a location away from the anchor site. The oxadiazole structural system of the compounds provide coordination bonds which improve the planarity of the π-conjugated backbone, thus providing the compounds of the present disclosure with favorable properties as organic dye material for a dye-sensitized solar cell.

The compounds of the present disclosure include:

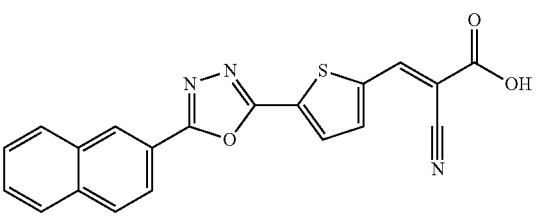

(Ia)

(E)-2-cyano-3-(5-(5-(naphthalen-2-yl)-1,3,4-oxadiazol-2-yl)thiophen-2-yl)cyanoacrylic acid

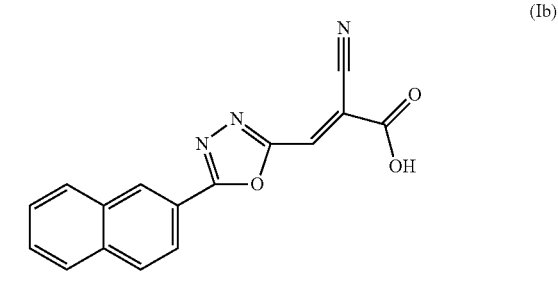

(Ib)

(E)-2-cyano-3-(5-(naphthalen-2-yl)-1,3,4-oxadiazol-2-yl)acrylic acid

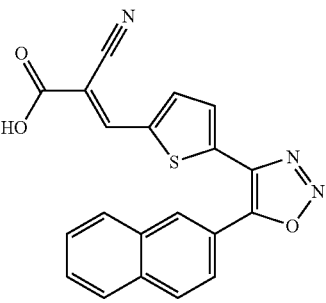

(IIa)

(E)-2-cyano-3-(5-(5-(naphthalen-2-yl)-1,2,3-oxadiazol-4-yl)thiophen-2-yl)cyanoacrylic acid (IIb)

(E)-2-cyano-3 (5-naphthalen-2-yl)-1,2,3-oxadiazol-4-yl)-acrylic acid

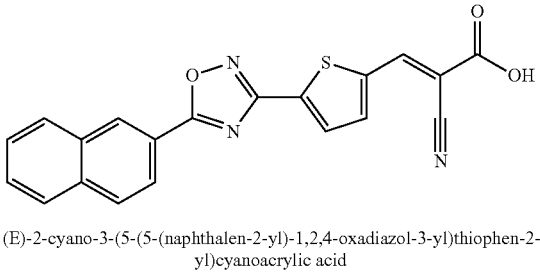

(IIIa)

(E)-2-cyano-3-(5-(5-(naphthalen-2-yl)-1,2,4-oxadiazol-3-yl)thiophen-2-yl)cyanoacrylic acid

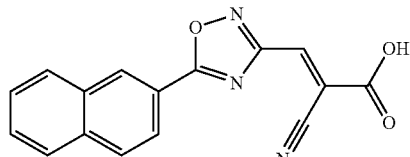

(E)-2-cyano-3-(5-(naphthalen-2-yl)-1,2,4-oxadiazol-3-yl)acrylic acid

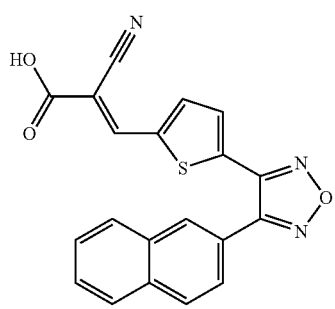

(E)-2-cyano-3-(5-(4-(naphthalen-2-yl)-1,2,5-oxadiazol-3-yl)thiophen-2-yl)acrylic acid

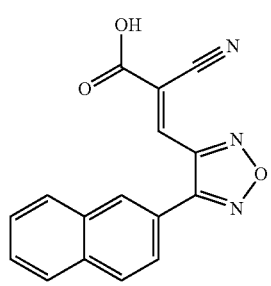

(E)-2-cyano-3-(4-(naphthalen-2-yl)-1,2,5-oxadiazol-3-yl)acrylic acid

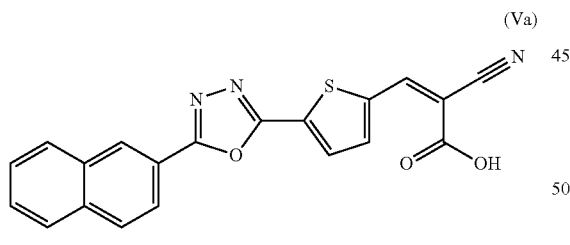

(Z)-2-cyano-3-(5-(5-(naphthalen-2-yl)-1,3,4-oxadiazol-2-yl)thiophen-2-yl)acrylic acid

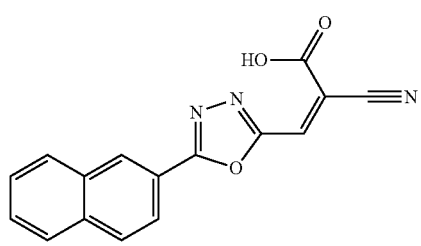

(Z)-2-cyano-3-(5-(naphthalen-2-yl)-1,3,4-oxadiazol-2-yl)acrylic acid

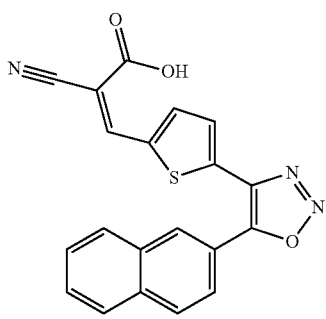

(Z)-2-cyano-3-(5-(5-(naphthalen-2-yl)-1,2,3-oxadiazol-4yl)thiophen-2-yl)acrylic acid

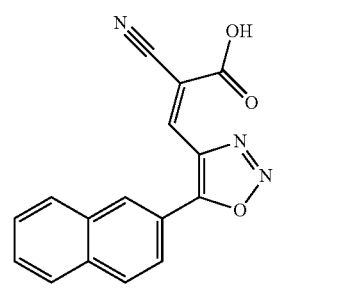

(Z)-2-cyano-3-(5-(naphthalen-2-yl)-1,2,3-oxadiazol-4-yl)acrylic acid

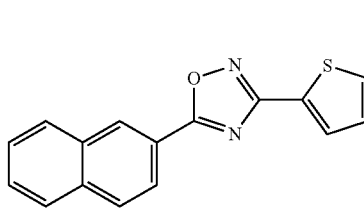

(Z)-2-cyano-3-(5-(5-(naphthalen-2-yl)-1,2,4-oxadiazol-3-yl)thiophen-2-yl)acrylic acid

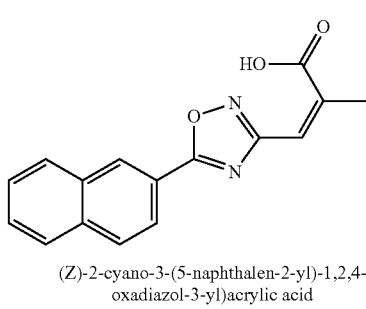

(Z)-2-cyano-3-(5-naphthalen-2-yl)-1,2,4-oxadiazol-3-yl)acrylic acid

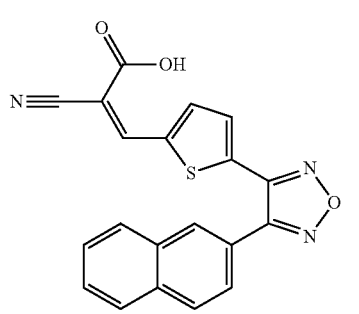

(Z)-2-cyano-3-(5-(4-(naphthalen-2-yl)-1,2,5-oxadiazol-3-yl)thiophen-2-yl)acrylic acid

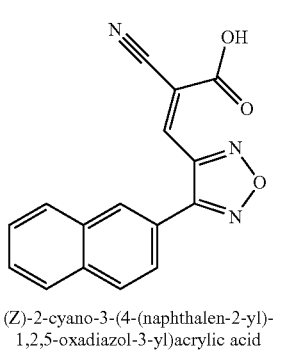

(VIIIb)

(Z)-2-cyano-3-(4-(naphthalen-2-yl)-
1,2,5-oxadiazol-3-yl)acrylic acid

It is within the scope of this disclosure to combine at least two of the light absorbing compounds with each other, such that a broader range of the solar spectrum may be harvested. Therefore mixtures of the dyes of the present disclosure when in use together will have absorption maxima at different wavelengths. In one embodiment, the dyes are mixed in a ratio of 1:1, 1:2, or 1:3 parts per weight %.

A dye sensitized solar cell comprising two or more dyes, may be referred to as a multiple-dye sensitized solar cell (M-DSSC). In one embodiment, the M-DSSC device may be built in a tandem geometry wherein the dyes are not mixed, but each is individually coated on at least two separate nanoporous layers and used in the device in at least two separate compartments.

At least one a dispersing medium may be used with the light absorbing compounds of the present disclosure. The dispersing medium may comprise an organic solvent selected from the group consisting of, but not limited to pentane, hexane, octane, benzene, toluene, xylene, diethyl ether, methanol, ethanol, isopropanol alcohol, acetone, ethyl acetate, butyl acetate, methyl ethyl ketone, acetonitrile, nitriles, propionitrile, dimethyl sulfoxide, triethylamine, acetic acid, propionic acid, methylene chloride, chloroform, and tetrahydrofuran, Studies were carried out to elucidate the role of the oxadiazole-based metal free photosensitizers and assist in the identification of additional organic dyes for DSSCs. The performance of each dye comprising a different oxadiazole isomer as a π-conjugated bridge was analyzed. DFT/TD-DFT calculations were performed using Amsterdam Density Functional (ADF) program 2013.01 to investigate the key parameters of light harvesting efficiency (LHE), free energy for electron injection ($\Delta G^{inject}$), excitation energies, and frontier molecular orbitals (FMOs).

Results from the studies indicate that the light absorbing molecules of the present disclosure will exhibit a more negative $\Delta G^{inject}$ concurrent with having a high LHE value. These parameters indicate that the molecules demonstrate a desirable IPCE, or incident photon to current efficiency.

Mechanisms of use and function may involve the direct attachment of the dye to a semiconductor surface, such as the $TiO_2$ surface, via the —COOH group of the cyanoacrylic group. The —CN group, having an electron acceptor character, positively effects electron injection from the dye to the semiconductor. Molecular orbital calculations indicate that in the ground state, the electron density is localized on the naphthyl group, located far away from the semiconductor surface. The naphthyl group is responsible for the light absorption abilities of the entire dye molecule. Furthermore, the theoretical HOMO of each of the series of compounds as disclosed herein is localized on the naphthyl group, whereas the LUMO is localized on the cyanoacrylic acid group. Electronic distribution over the oxadiazole unit, and in one embodiment, the additional thiophene unit, in both HOMO and LUMO shows that an effective photodriven charge transfer excitation can take place through this planar bridge. The electronic distribution of the HOMO and LUMO levels are well separated and the transition between these two can be considered as a charge transfer excitation.

Additional calculations were performed to illustrate the oscillator strength of the proposed compounds, shown in FIG. 2. In spectroscopy, oscillator strength is defined as a dimensionless quantity that expresses the probability of absorption or emission of electromagnetic radiation in transitions between energy levels of an atom or molecule.

The examples below are intended to further illustrate the various embodiments of the oxadiazole-containing dyes, and are not intended to limit the scope of the claims.

Example 1

The performance of DSSCs evaluated by IPCE:
IPCE is associated with charge collection efficiency ($\eta_c$), electron injection efficiency ($\phi_{injc}$) and light harvesting efficiency (LHE), as:

$$IPCE = LHE \times \phi_{injc} \times \eta c \quad (1)$$

LHE can be calculated in the following way:

$$LHE = 1 - 10^{-f} \quad (2)$$

where "f" is the absorption of dye associated with maximum absorption also called oscillator strength and $\phi_{injc}$ is related to the free energy of electron injection as:

$$\phi injc \alpha f(-\Delta G inject) \quad (3)$$

Eq-3 shows that the more negative $\Delta G^{inject}$, the greater the electron injection efficiency.

$\Delta G^{inject}$ is the difference between the oxidation potential energy of the excited state ($E_{ox}^{dye*}$) and the reduction potential energy of the $TiO_2$ conduction band ($E_{CB}$), which can be described as:

$$\Delta G_{inject} = E_{ox}^{dye*} - E_{CB} \quad (4)$$

Similarly, $E_{ox}^{dye*}$ can be calculated using the following equation:

$$E_{ox}^{dye*} = E_{ox}^{dye} - \Delta E \quad (5)$$

where $E_{ox}^{dye}$ (—HOMO) is the dye ground state oxidation potential and $\Delta E$ is the lowest absorption energy associated with $\lambda_{max}$.

Computational Detail

All DFT/TD-DFT calculations were performed using the Amsterdam Density Functional (ADF) program (2013.01). The ground state geometries of each of the series of oxadiazole dyes were optimized by applying the hybrid B3LYP level together with a triple-ζ polarization basis function. The UV-Vis spectrum of each of the series of oxadiazole dyes was simulated in an ethanol solvent. The conductor-like screening model (COSMO) was utilized to take into account any effects attributable to the solvent. Excitation energies were examined using both TD-DFT and the statistical averages of orbital potentials (SAOP) models. These examination models also took into account any effects attributable to the solvent system. In all the calculations, the relativistic effects were taken into account by the zero order regular approximation (ZORA) Hamiltonian in its scalar approximation. As understood, the zeroth order regular approximation (ZORA) to the Dirac equation accurately and efficiently treats relativistic effects in chemistry. ZORA can be applied with spin-orbit coupling or as scalar correction only.

Designed Oxadiazole-based Dyes

The structures of the oxadiazole-containing dyes are shown in FIG. 1. In these structures, a naphthalene group is designated as the electron-donating moiety and carboxyl and cyano groups (—COOH and —CN) are introduced as electron acceptor and anchor groups due to their electron-withdrawing ability and bonding ability, respectively. The oxadiazole isomers were each individually introduced as π-conjugation groups in order to bridge the donor-acceptor systems. A double bond and a thiophene unit were also introduced to the π-conjugation system for the fine tuning of molecular planar configurations, and to broaden the absorption spectra of the dye molecules.

Initial quantum-chemical calculations using density functional theory and time dependent density functional theory (DFT/TDDFT) indicates that the oxadiazole compounds maintain a planar geometry in the ground state that, together with the position of the naphthyl moiety favors efficient π-π stacking of the acceptor molecules and enhances the electron mobility in the π-π direction. As a solvent, common organic solvents such as water, but preferably ethanol, methanol, and butanol, may be used. For the theoretical calculations, ethanol was used as the theoretical solvent.

Table.1 shows the HOMOs, LUMOs and HOMO-LUMO energy gaps of the compounds of the disclosure. As previously discussed, the HOMO, LUMO, and band gap energies of photosensitizers play important roles in providing the thermodynamic driving force for electron injection. In order to obtain an efficient charge transfer, the LUMOs of the dye must be more negative than the conduction band of the semiconductor, while the HOMO level must be more positive than the redox potential of the electrolyte. These results obtained from the computational studies suggest that each of the dye comprising the (E) enantiomer of the oxadiazole isomer dye further comprising a thiophene group, of formula Ia, IIa, IIIa, and IVa, are capable of injecting electrons into the conduction bands of $TiO_2$.

TABLE 1

The FMO (eV) and H-L$_{gap}$ (eV) energies of systems 1-4

| Photosensitizer | LUMO | HOMO | H-L$_{GAP}$ |
|---|---|---|---|
| (Ia) | −3.956 | −5.657 | 1.701 |
| (IIa) | −3.625 | −5.582 | 1.957 |
| (IIIa) | −3.767 | −5.808 | 2.041 |
| (IVa) | −3.802 | −5.827 | 2.025 |

TABLE 2

The ground state potential $E_{ox}^{dye}$ (eV), excited state potential $E_{ox}^{dye*}$ (eV), lowest absorption energy ΔE (eV), maximum absorption $\lambda_{max}$ (nm), oscillating strength (f) and transition character.

| Dyes | $E_{ox}^{dye}$ | $E_{ox}^{dye*}$ | ΔE | $\lambda_{max}$ | f | Main Transition → |
|---|---|---|---|---|---|---|
| (Ia) | 5.657 | 3.296 | 2.361 | 525 | 0.764 | H-1 → L (82.4%) |
| (IIa) | 5.583 | 3.133 | 2.450 | 507 | 0.722 | H-1 → L (69%) |
| (IIIa) | 5.808 | 3.118 | 2.620 | 473 | 0.865 | H-1 → L (57%) |
| (IVa) | 5.827 | 3.258 | 2.569 | 483 | 0.780 | H-1 → L (68%) |

LHE and $\Delta G^{inject}$ can be calculated by using equation-2 and equation-4 respectively. The results are tabulated in Table 3. It can be found from Table 3 that all the $\Delta G^{inject}$ values calculated are negative, indicating that the conduction band edge of $TiO_2$ lies below the excited state of the dyes, and thus favors the electron injection. As illustrated in Table 3, there is only a slight difference in the LHE values between Dyes (I)-(IV), indicating that each of the photosensitizers as disclosed herein all generate comparable photocurrent values.

TABLE 3

Free energy of electron injection $\Delta G^{inject}$ (eV) and Light harvesting efficiency LHE

| Photosensitizer | $\Delta G^{inject}$ | LHE |
|---|---|---|
| (Ia) | −0.704 | 82 |
| (IIa) | −0.867 | 80 |
| (IIIa) | −0.882 | 86 |
| (IVa) | −0.742 | 83 |

The simulated absorption spectra of Systems 1-4 are shown in FIG. 1. The absorption spectra of each dye of the series of dye comprises two regions consisting of a first intense peak in the region of 326 nm-450 nm and second peak in the region of 472 nm-700 nm. The dye comprising the 1,3,4-oxadiazole bridge displays a broader peak when compared to the dyes comprising the remaining oxadiazole isomers in the series of dyes. The ground and excited state potential ($E_{ox}^{dye}$), maximum absorption ($\lambda_{max}$), oscillation strength (f) and main transitions are all presented in Table 2.

Figure 3:
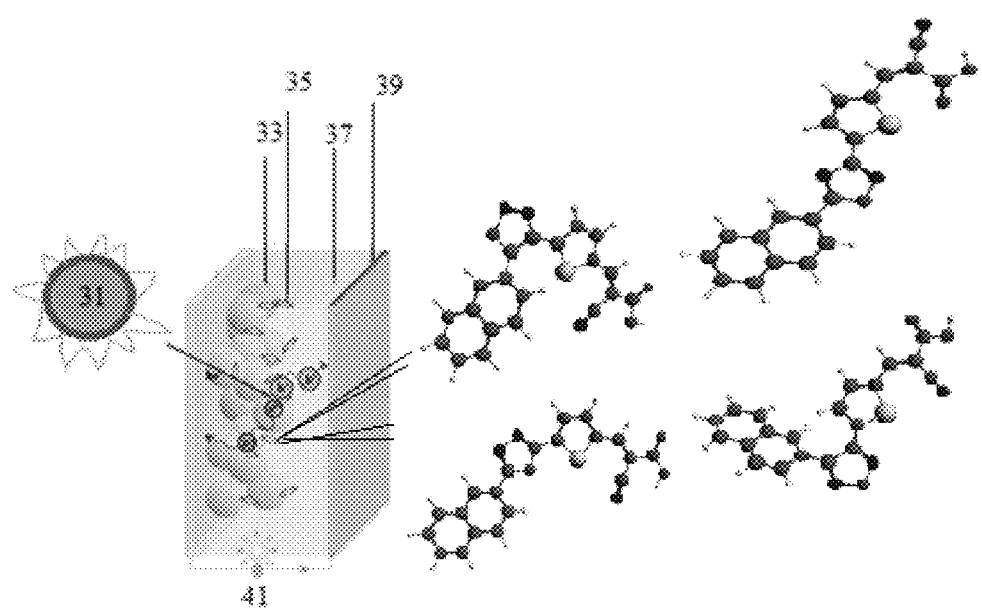
FIG. 3 shows the structure of a dye sensitized solar cell incorporating at least one of an (E) structure of the dye (Ia, IIa, IIIa, IVa) comprising an oxadiazole isomer, a naphthyl group and a thiophene group.

The construction of a DSSC is well known to a person skilled in the art, and herein, the DSSC for use comprises at least one of the series of oxadiazole dye as disclosed, an anode, a cathode, and an electrolyte. The anode and cathode are arranged in a sandwich-like configuration, and the electrolyte is inserted between the two electrodes. A proposed structure for a DSSC incorporating at least one of the series of light absorbing molecules, or light absorbing photosensitizers, is shown in FIG. 3.

The cathode 39 comprises an electrically conductive substrate, such as a transparent glass comprising an oxide selected from the group consisting of, but not limited to, titanium dioxide, zinc oxide, tin oxide, or indium-tin oxide (ITO).

The anode comprises an electrically conductive substrate, such as a transparent glass and a semiconducting layer comprising a semiconductor 33 and at least one of the series of oxadiazole dye 35 as disclosed adsorbed thereto. Materials for the semiconductor include, but are not limited to, metal oxides such as titanium oxides, niobium oxides, zinc oxides, tin oxides, tungsten oxides, $TiOF_2$, and indium oxides, preferably $TiO_2$, while an electrolytic solution 37 is generally based on an iodine redox couple ($I^-/I_3^-$). Light is supplied from a light source, such as the sun 31 and transformation of solar energy to electrical energy is shown by the arrow 41.

The light absorbing oxadiazole compounds as disclosed herein are preferably adsorbed onto the semiconductor via contact of the dye. The dye and the semiconductor surface maintain contact through a chemical bond between the anchoring group of the dye and the semiconductor material.

Any aggregation of the dye molecules tends to reduce the efficiencies of the DSSCs. Therefore, in one embodiment, it is desirable to include a bulky chemical compound in the dye solution so as to improve the solubility of the dye, and prevent the dye molecules from aggregating. Chemical groups can be selected from the group consisting of, but not limited to, the compounds of the current disclosure without their binding anchor group.

Further advantages over the prior art involve the ability of the dye color in determining the wavelength of light that the solar cell can capture. Any adjustment to the dye structure and/or color will influence the performance of the device. Many dyes reflect red light, and, when coupled with an oxide such as titanium oxide (white), appear 'pink'. However, the series of light absorbing molecules as disclosed herein absorb light in several ranges so there exists the possibility of choosing a different coloring of the dye sensitized solar cell device in relation to the application type.

The use of the light absorbing molecules of this disclosure as dyes in dye sensitized solar cell applications include a variety of electronic devices. These devices include energy supply devices for mobile phones, notebooks, laptops, portable audio-tape players, MP3-players, remote controls, e-cards, e-books, e-readers, portable CD players, portable DVD players, cameras, digicams, GPS devices, portable sensors, and portable solar chargers for batteries of any of the aforementioned devices. As organic dyes have high absorption coefficients, a lesser amount of dye is able to absorb the same amount of light. A lower, or lesser amount of one dye on a surface enables the use of more dyes with different absorption properties, ideally being a mixture of dyes absorbing the entire range of the solar spectrum.

The compounds of the current disclosure may have further applications in the field of photodynamic therapy. As the light absorbing compounds disclosed herein contains few atoms and absorb in the longer wavelength regions thus providing for use in photodynamic therapies for the treatment of malignant, diseased, hypo- and/or hyper-proliferative cells and/or tissues. Formulations or compositions comprising at least one of the oxadiazole compounds as disclosed herein may act as a photopharmaceutical for treating conditions such as, but not limited to cancer, benign tumors, skin infections, and even a lack or reduction of hair growth.

During a photodynamic therapy (PDT) treatment, at least one of the light absorbing compounds may be supplied to an area of the body in need of treatment. The area is then exposed to light of a suitable frequency and intensity necessary to activate the photopharmaceutical so as to cause necrosis, or apoptosis of the targeted tissue. In a further embodiment, a stimulation of a hypo-proliferative tissue may occur.

Administration of Photosensitizers

The light absorbing compounds may be administered as a topical or subcutaneous preparation, or by localized administration in the form of an intradermal injection or an implant. The light absorbing compounds may be administered by means including, but not limited to, topical lotions, topical creams, topical pastes, topical suspensions, or a local administration in the form of intradermal injection or an implant. A preferred method of administration is to apply the light absorbing compounds topically in an excipient containing a solubilizing agent. For topical formulations (such as ointments) to be applied to the surface of the skin, the concentration of the light absorbing compound in the excipient preferably ranges from about 0.001 to about 10% w/w, and more preferably from about 0.005 to about 5% w/w, and even more preferably between about 0.01 to about 1% w/w. Particularly preferred is the use of about a 0.2% w/w topical formulation.

The dose of light absorbing compound may be determined by factors such as, but not limited to, the light absorbing compound chosen, the physical delivery system in which it is carried, the individual subject, and the target tissue to be treated. The dose should also be adjusted with respect to parameters, such as irradiance, duration of the light used in PDT, and time interval between administration of the dose and the therapeutic irradiation. Depending on the specificity of the preparation, smaller or larger doses of photosensitizers may be needed. For compositions which are highly specific to the target skin tissues and cells. The potency of the light absorbing compound also determines the dosage, with less required for highly potent light absorbing compounds, and more for light absorbing compounds with less potency. For topical formulations (such as ointments) to be applied to the surface of the skin, the concentration of the light absorbing compound in the excipient can range from about 0.001 to about 10% w/w, preferably from about 0.005 to about 5% w/w (or about 0.05 to about 1% w/w), and even more preferably between about 0.1 to about 1% w/w.

Each light absorbing compound requires activation with an appropriate wavelength(s) of electromagnetic radiation. As such, the methods of the invention may be conducted with any irradiation, preferably with light, which activates the light absorbing compound used. Preferably, the irradiation contains one or more wavelength which is capable of penetrating the skin to activate the light absorbing compound used. The wavelength(s) of radiation or light useful in the invention depends on the activation range of the light absorbing compound used as part of the treatment method. In one embodiment the wavelengths range from 326-700 nanometers (nm). Depending upon the light absorbing compound and upon the desired depth of targeted tissue penetration, the preferred wavelengths range from about 500 to about 700 nm. The oxadiazole light absorbing compounds may be activated by a red light, as well as ambient light containing wavelengths from 326 nm-700 nm. Light having a wavelength shorter than 400 nm may be considered acceptable, but not preferred because of the potentially damaging effects of UVA light.

Any appropriate activation energy source, depending on the absorption spectrum of the light absorbing compound, may be used for activation. Preferred sources include, but are not limited to, lasers, light emitting diodes (LED), incandescent lamps, arc lamps, standard fluorescent lamps, U.V. lamps, and combinations thereof. More preferred are lasers, light emitting diodes, and combinations thereof Alternatively, any convenient source of activation energy having a component of wavelengths that are absorbed by the light absorbing compound may be used, for example, an operating room lamp, or any bright light source, including sunlight. Wavelengths in the ultraviolet range are not preferred as they may lead to a mutagenic event. Therefore, the activation energy used for the methods herein is not in the ultraviolet range.

The activation energy dose administered during the PDT treatment contemplated herein can vary as necessary. Preferably, for light absorbing compounds of high potency, the dosage of the light is approximately 25-200 $J/cm^2$ for a topically-delivered photosensitizers. It is recommended that the total dose of the irradiation should not exceed 200 $J/cm^2$, more preferably not to exceed 100 $J/cm^2$. For administering the light absorbing compound the preferred doses can range between about 0.01 $J/cm^2$ to about 200 $J/cm^2$, more preferably 0.1 $J/cm^2$ to about 100 $j/cm^2$. Increases in irradiance will generally decrease the light exposure times. Generally, a higher dose of photosensitizer will also decrease the light dose required to exert a therapeutic effect.

The intensity of the light source should not exceed about 600-1000 $mW/cm^2$. Irradiances between about 10 and about 400 $mW/cm^2$, are preferred; more preferably are those between about 25 and about 100 $mW/cm^2$.

The irradiation may last from about 10 seconds to about 3 hours, preferably between 1 minute and 90 minutes. Irradiation times of between 5 minutes and 10 minutes may be used. The irradiation or light exposure as disclosed may be directed to a small or large area of the body or scalp depending on the tissue to be treated. Treatment may be preceded with an assessment of the time of light exposure for the patient's minimal erythemal dose (MED) occurrence in order to avoid potential burning of the exposed skin.

The PDT may be a single treatment, but it is preferred that the treatment is repeated. The frequency may vary. For example, the treatments may be daily, twice weekly, weekly, every two weeks, monthly, every six weeks, every two months, quarterly, twice annually, or annually, or other suitable time interval to treat or maintain a targeted tissue's prevailing condition. The total number of treatments of a specifically targeted tissue can range from one to twenty. In cases where hair loss is observed, maintenance treatment on a regular basis may be initiated and sustained. It is preferred that the total number of treatments in any one-month period be from 1 to 12, more preferably from 2 to 4.

The time between administration of light absorbing compound and administration of activation energy will vary depending on a number of factors. Activation energy delivery can take place at any suitable time following administration of light absorbing compound as long as there is still light absorbing compound present at the skin. Activation energy treatment within a period of about five minutes to about 5 hours after administration of the light absorbing compound is preferred, with a range of 15 minutes to 90 minutes being more preferable. Even more preferably the light is administered within a period of about 30-45 minutes after administration of the light absorbing compound. Light absorbing compounds that may rapidly accumulate in target tissues can be activated soon after administration. Also, light absorbing compounds that may be metabolically cleared from tissues quickly should be activated soon after accumulation in the target tissues.

The light absorbing compounds disclosed herein may be formulated into a variety of compositions. These compositions may comprise any component that is suitable for the intended purpose, such as conventional delivery vehicles and excipients including isotonising agents, pH regulators, solvents, solubilizers, dyes, gelling agents and thickeners and buffers and combinations thereof. Suitable excipients for use with light absorbing compounds include water, saline, dextrose, glycerol and the like.

Typically, the light absorbing compound is formulated by mixing it, at an appropriate temperature, e.g., at ambient temperatures, and at appropriate pHs, and the desired degree of purity, with one or more physiologically acceptable carriers, i.e., carriers that are nontoxic at the dosages and concentrations employed. The pH of the formulation preferably ranges anywhere from about 3 to about 8, preferably in the physiological range of 6.5 to 7.5.

The formulations may comprise a skin-penetration enhancer selected from the group consisting of glycol ethers, fatty acids, fatty acid esters, glycol esters, glycerides, azones, polysorbates, alcohols, dimethylsulfoxide, and mixtures thereof.

Solvents acceptable for use in the treatment include, but are not limited to, DMSO (dimethylsulfoxide), polyethylene glycol (PEG), ethanol, and methyl alcohol, while solubilizers such as, but not limited to titanium dioxide, polyethylene glycol, propylene glycol, polysorbates, and mixtures thereof may also be added at a percentage of 10% to 70% by weight.

It is preferred that the formulations have a viscosity at 20° C. of from about 50 cps to about 50000 cps, more preferably from about 500 cps to about 40000 cps, even more preferably from about 5000 cps to about 30000 cps. Viscosity modifiers can be selected from the group consisting of but not limited to polyethylene glycols, waxes, saturated $C_8$-$C_{18}$ fatty acid glycerides, xantham gum, polyvinyl alcohol, and mixtures thereof.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A dye sensitized solar cell, comprising:
an anode,
a cathode,
a light absorbing layer between the anode and the cathode,
wherein the light absorbing layer comprises a semiconductor and a light absorbing compound,
wherein the light absorbing compound is chemisorbed on the semiconductor; and
wherein the light absorbing compound has formula (I):

wherein $A_1$ is a divalent thiophene group of formula (I')

$A_2$ is a divalent 5-membered heterocyclic group of formula (II'), (III'), (IV'), or (V'):

-continued

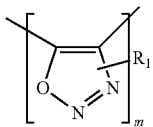 (IV')

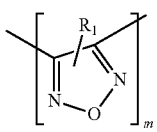 (V')

$A_3$ is an aromatic hydrocarbon chromophore of formula (VI'), (VII'), or (VIII')

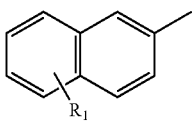 (VI')

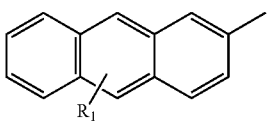 (VII')

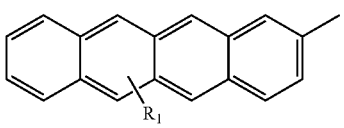 (VIII')

wherein $R_1$ is H, OH, C1-C6 alkyl, Cl, Br, F, or I, m is from 1-5, and n is from 0-5.

2. The dye sensitized solar cell of claim 1, wherein the light absorbing compound of formula (I) is an (E) isomer.

3. The dye sensitized solar cell of claim 1, wherein the light absorbing compound of formula (I) is a (Z) isomer.

4. The dye sensitized solar cell of claim 1, wherein the light absorbing compound is selected from the group consisting of:

(E)-2-Cyano-3-(5-(5-(naphthalen-2-yl)-1,3,4-oxadiazol-2-yl)thiophen-2-yl)-acrylic acid;
(E)-2-Cyano-3-(5-(5-(naphthalen-2-yl)-1,2,3-oxadiazol-4-yl)thiophen-2-yl)-acrylic acid;
(E)-2-Cyano-3-(5-(5-(naphthalen-2-yl)-1,2,4-oxadiazol-3-yl)thiophen-2yl)-acrylic acid;
(E)-2-Cyano-3-(5-(4-(naphthalen-2-yl)-1,2,5-oxadiazol-3-yl)thiophen-2yl)-acrylic acid;
(E)-2-Cyano-3-(5-(naphthalen-2-yl)-1,3,4-oxadiazol-2-yl)-acrylic acid;
(E)-2-Cyano-3-(5-(naphthalen-2-yl)-1,2,3-oxadiazol-4-yl)-acrylic acid;
(E)-2-Cyano-3-(5-(naphthalen-2-yl)-1,2,4-oxadiazol-3-yl)-acrylic acid;
(E)-2-Cyano-3-(4-(naphthalen-2-yl)-1,2,5-oxadiazol-3-yl)-acrylic acid;
(Z)-2-Cyano-3-(5-(5-(naphthalen-2-yl)-1,3,4-oxadiazol-2-yl)thiophen-2-yl)-acrylic acid;
(Z)-2-Cyano-3-(5-(5-(naphthalen-2-yl)-1,2,3-oxadiazol-4-yl)thiophen-2-yl)-acrylic acid;
(Z)-2-Cyano-3-(5-(5-(naphthalen-2-yl)-1,2,4-oxadiazol-3-yl)thiophen-2yl)-acrylic acid;
(Z)-2-Cyano-3-(5-(4-(naphthalen-2-yl)-1,2,5-oxadiazol-3-yl)thiophen-2yl)-acrylic acid;
(Z)-2-Cyano-3-(5-(naphthalen-2-yl)-1,3,4-oxadiazol-2-yl)-acrylic acid;
(Z)-2-Cyano-3-(5-(naphthalen-2-yl)-1,2,3-oxadiazol-4-yl)-acrylic acid;
(Z)-2-Cyano-3-(5-(naphthalen-2-yl)-1,2,4-oxadiazol-3-yl)-acrylic acid; and
(Z)-2-Cyano-3-(4-(naphthalen-2-yl)-1,2,5-oxadiazol-3-yl)-acrylic acid.

5. The dye sensitized solar cell of claim 1, wherein the light absorbing compound is represented by formula (Ia)

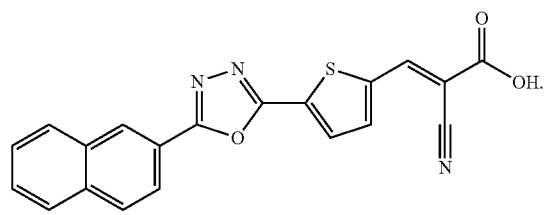 (Ia)

6. The dye sensitized solar cell of claim 1, wherein the light absorbing compound is represented by formula (Ib)

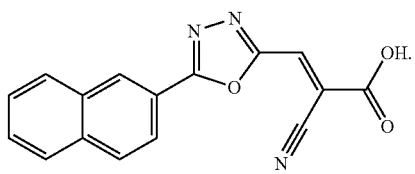 (Ib)

7. The dye sensitized solar cell of claim 1, wherein the light absorbing compound is represented by formula (IIa)

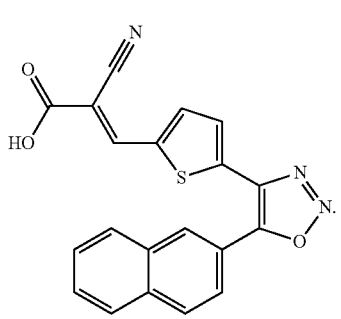 (IIa)

8. The dye sensitized solar cell of claim 1, wherein the light absorbing compound is represented by formula (IIb)

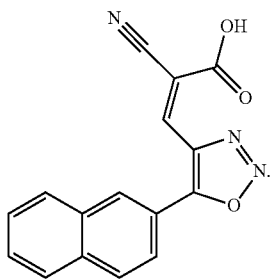

9. The dye sensitized solar cell of claim 1, wherein the light absorbing compound is represented by formula (IIIa)

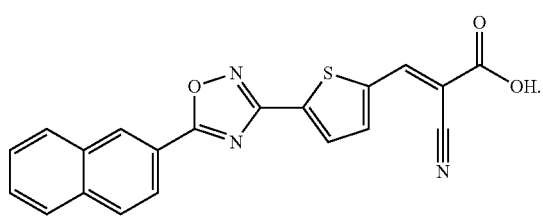

10. The dye sensitized solar cell of claim 1, wherein the light absorbing compound is represented by formula (IIIb)

(IIIb)

11. The dye sensitized solar cell of claim 1, wherein the light absorbing compound is represented by formula (IVa)

(IVa)

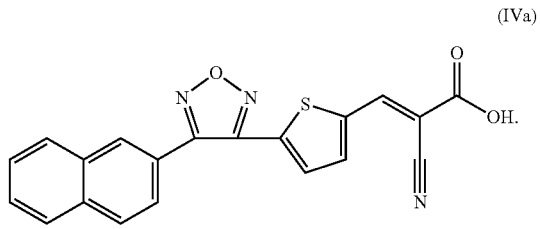 [SMILES: N#C/C(=C\c1ccc(-c2nonc2-c2ccc3ccccc3c2)s1)C(=O)O]

12. The dye sensitized solar cell of claim 1, wherein the light absorbing compound is represented by formula (IVb)

(IVb)

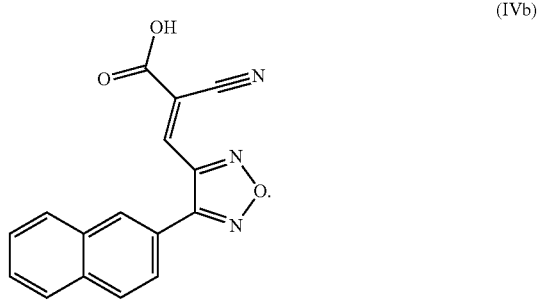 [SMILES: N#C/C(=C\c1nonc1-c1ccc2ccccc2c1)C(=O)O]

13. The dye sensitized solar cell of claim 1, further comprising:

a passive substrate.

* * * * *